US007000469B2

(12) United States Patent
Foxlin et al.

(10) Patent No.: US 7,000,469 B2
(45) Date of Patent: *Feb. 21, 2006

(54) MOTION-TRACKING (75) Inventors: Eric Foxlin, Arlington, MA (US); Yury Altshuler, Dedham, MA (US)

(73) Assignee: Intersense, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/762,810

(22) Filed: Jan. 22, 2004

(65) Prior Publication Data

US 2004/0149036 A1 Aug. 5, 2004

Related U.S. Application Data

(63) Continuation-in-part of application No. 10/224,901, filed on Aug. 21, 2002, now Pat. No. 6,681,629, which is a continuation of application No. 09/556,135, filed on Apr. 21, 2000, now Pat. No. 6,474,159.

(51) Int. Cl.
*G01P 15/00* (2006.01)

(52) U.S. Cl. .................................................. 73/488
(58) Field of Classification Search .................. 73/510, 73/511, 514.02, 488, 503.3; 702/94, 150; 356/623
See application file for complete search history.

(56) References Cited

U.S. PATENT DOCUMENTS

| 5,645,077 A | 7/1997 | Foxlin |
| 6,176,837 B1 | 1/2001 | Foxlin |
| 6,474,159 B1 | 11/2002 | Foxlin et al. |

FOREIGN PATENT DOCUMENTS

| DE | 198 30 359 A1 | 1/2000 |
| DE | 198 30 359 | 1/2000 |
| JP | 2001103395 | 4/2001 |

OTHER PUBLICATIONS

Foxlin, E. "Head–tracking relative to a moving vehicle or simulator platform using differential inertial sensors." Erratum to Proceedings of SPIE 4021: 133–144, 2000. XP008029663.
E. Foxlin, "Head–tracking relative to a moving vehicle or simulator platform using differential inertial sensors".
E. Fuchs, "Inertial head–tracking", M.S. Thesis, Dept. of E.E.C.S., MIT, 1993.
E. Foxlin, "Inertial head–tracker sensor fusion by a complementary separate–bias kalman filter", Proc. VRAIS '96 Virtual Reality Annual Intl. Symposium, Santa Clara, CA 1996.
E. Foxlin et al., "Miniature 6–DOF inertial system for tracking HMDs", SPIE vol. 3362, Proc. AeroSense '98 Conference on Helmet– and Head–Mounted Displays III, Orlando, FL 1998.
InterSense Inc. homepage—http://www.isense.com.
K. Britting, "Inertial navigations systems analysis", New York, Wiley Interscience, 1971.
C. Broxmeyer, "Inertial navigation systems", New York, McGraw–Hill, 1964.
R. Parvin, "Inertial Navigation", Princeton, New Jersey, Van Nostrand, 1962.
R.G. Brown et al., "Introduction to random signals and applied Kalman filtering", $2^{nd}$ edition, New York, John Wiley & Sons, 1992.

*Primary Examiner*—Helen Kwok
(74) *Attorney, Agent, or Firm*—Fish & Richardson P.C.

(57) ABSTRACT

A system for tracking the motion of an object relative to a moving reference frame includes a first inertial sensor mounted on the tracked object; a second inertial sensor mounted on the moving reference frame; a third inertial sensor mounted on the moving reference frame and spaced apart from the second inertial sensor; and an element coupled to said first and second and third inertial sensors and configured to determine a position of the object relative to the moving reference frame based on the signals from the first and second and third inertial sensor.

45 Claims, 9 Drawing Sheets

MOTION-TRACKING

This application is a continuation-in-part of U.S. application Ser. No. 10/224,901, filed on Aug. 21, 2002 now U.S. Pat. No. 6,681,629, which is a continuation of U.S. application Ser. No. 09/556,135 filed on Apr. 21, 2000, issued on Nov. 5, 2002 as U.S. Pat. No. 6,474,159. The disclosure of these applications are incorporated herein by reference.

TECHNICAL FIELD

This invention relates to motion tracking.

BACKGROUND

Inertial tracking with automatic drift correction has been demonstrated to be a successful technique for tracking objects, such as limbs, cameras, input devices, or head mounted displays (HMDs), offering low jitter, fast response, increased range, and reduced problems due to interference or line-of-sight occlusion. Inertial trackers have been successfully applied to a wide range of HMD applications including virtual environment (VE) training, virtual prototyping, interactive visualization and design, VR gaming, and even fixed-base vehicle simulation. Within this gamut of applications, inertial trackers have gained widespread acceptance as a high-performance, robust and cost-effective alternatives to magnetic, optical and acoustic tracking systems. InterSense of Burlington, Mass., has pioneered the commercial development of motion tracking systems using miniature MEMS-based inertial sensors, and now offers a broad product line of inertial hybrid trackers .

Until now, inertial trackers have not been used in applications that require tracking motion relative to a moving platform instead of relative to the earth. This includes such important applications as motion-base driving and flight simulators, conventional VE systems deployed on board ships, and a range of live vehicular applications such as driver's or pilot's vision enhancement, helmet-mounted cueing systems, and advanced human-machine interfaces to improve pilots' situational awareness and control capability. People wishing to use inertial trackers in these types of applications have been realized that standard inertial tracking systems such as the InterSense IS-300, 600 or 900 will not function correctly if operated on a moving platform such as a motion-base simulator or vehicle. The inertial sensors would measure head motion relative to the ground, while the drift-correcting range sensors would measure head pose relative to the vehicle platform in which the reference receivers are mounted. While the vehicle is turning or accelerating, the Kalman filter would attempt to fuse inconsistent data and produce unpredictable results.

SUMMARY

In general, in one aspect, the invention features a system for tracking the motion of an object relative to a moving reference frame. The system includes a first inertial sensor mounted on the tracked object; a second inertial sensor mounted on the moving reference frame; a third inertial sensor mounted on the moving reference frame and spaced apart from the second inertial sensor; and an element coupled to said first and second and third inertial sensors and configured to determine a position of the object relative to the moving reference frame based on the signals from the first and second and third inertial sensor.

Implementations of the invention may include one or more of the following features. The determination of the position of the object includes determination of at least one component of the angular acceleration of the moving reference frame. The determination of angular acceleration is made by combining linear acceleration data from the second and third inertial sensors. A non-inertial measuring subsystem may make independent measurements related to the position of the object relative to the moving reference frame, and use them for correcting any drift that may occur in the inertial orientation integration. The non-inertial measuring subsystem may be selected from the set of optical, acoustic, magnetic, RF, or electromagnetic technologies.

The non-inertial measuring system may be optical and involve measurement of the location of one or more targets in the image planes of one or more sensors. The targets may emit radiation within a defined bandwidth about a central wavelength selected in the infrared, visible or ultraviolet region of the electromagnetic spectrum. The central wavelength may be substantially invisible to night vision equipment. The central wavelength may be substantially invisible to the human eye. At least one optical sensor may be mounted on the tracked object. At least one optical sensor may be mounted rigidly with respect to the moving reference frame. The optical system may include two sensors mounted rigidly with respect to the moving reference frame, and separated by at least 10 centimeters. The second inertial sensor may be physically packaged with one of the optical sensors, and the third inertial sensor may be physically packaged with the other optical sensor.

In general, in another aspect, the invention provides a system for tracking the motion of an object relative to a moving reference frame including a first inertial sensor mounted on the tracked object; a second inertial sensor mounted on the moving reference frame; a third inertial sensor mounted on the moving reference frame and spaced apart from the second inertial sensor; a third inertial sensor mounted on the moving reference frame and spaced apart from the second inertial sensor; an element coupled to said first and second and third inertial sensors and configured to determine a position of the object relative to the moving reference frame based on the signals from the first and second and third inertial sensor; and a drift corrector for correcting inertial drift in the determined orientation of the object with respect to the moving reference frame. The drift corrector may include a Kalman filter.

In general, in another aspect, the invention provides a system for tracking the motion of an object relative to a moving reference frame including a first motion sensing means mounted on the tracked object; a second motion sensing means mounted on the moving reference frame; a means coupled to said first and second inertial sensors for determining an orientation of the object relative to the moving reference frame based on the signals from the first and second motion sensing means; and a drift corrector for correcting inertial drift in the determined orientation of the object with respect to the moving reference frame, where the drift corrector includes a Kalman filter.

In general, in another aspect, the invention provides a method for tracking the motion of an object relative to a moving reference frame including mounting a first inertial sensor on the tracked object; mounting a second inertial sensor on the moving reference frame; determining an orientation of the object relative to the moving reference frame based on the signals from the first and second inertial sensors; and correcting inertial drift in the determined orientation of the object with respect to the moving reference frame, using a Kalman filter.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

1 Derivation of Kinematics 1.1 Inertial Tracking Relative to Fixed Platform

Figure 1:
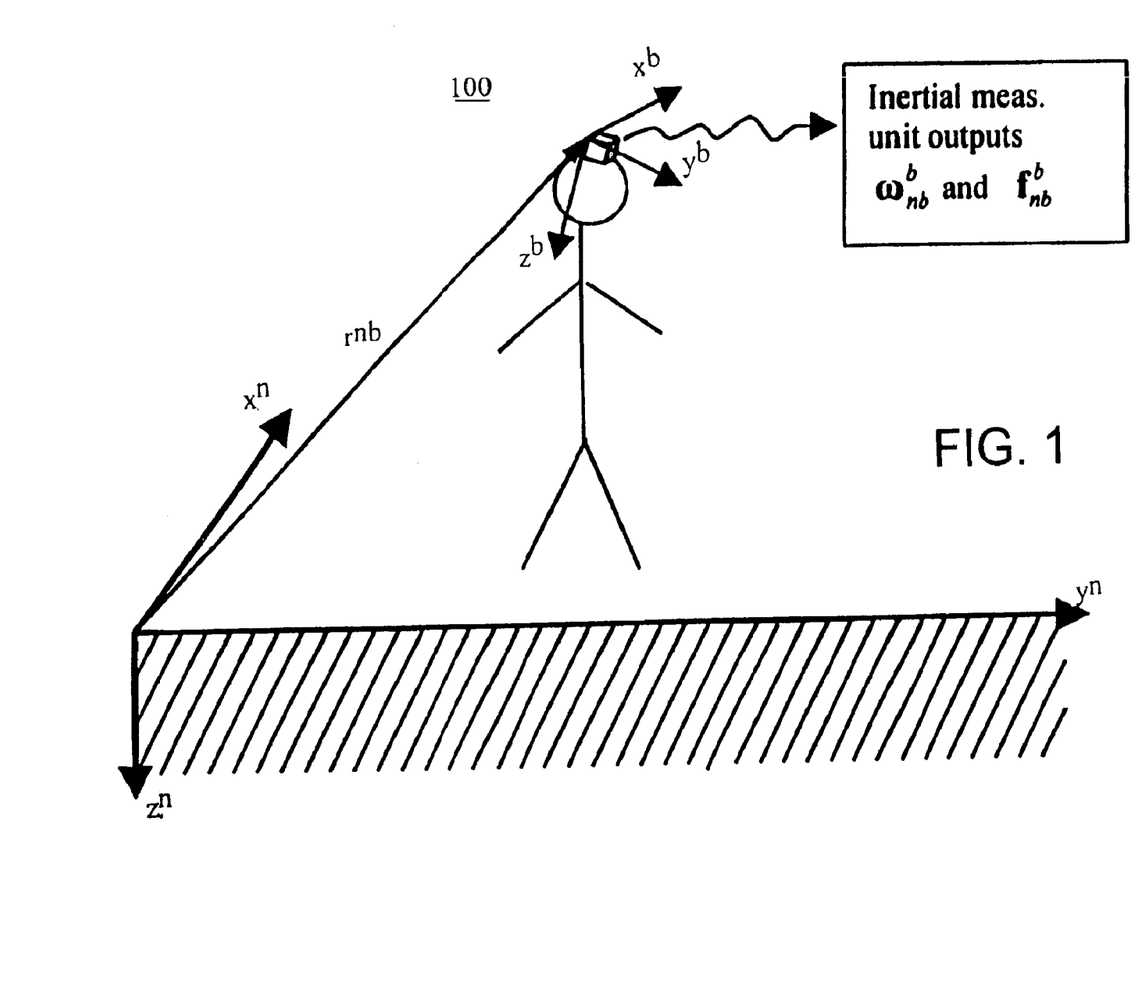
FIG. 1 shows inertial tracking relative to stationary ground.

FIG. 1 illustrates the case of using an inertial system 100 to track the pose of a body, b, with respect to an inertially fixed navigation frame, n. In this situation, which represents the operation of InterSense's existing tracking products, there are only two coordinate frames used. Hereafter, vectors and matrices are designated with boldface characters, and superscripts, if present, indicate in which frame vectors are coordinatized. The subscripts on $r_{nb}$ indicate that it is the vector from the n-frame origin to the b-frame origin. Likewise $\omega_{nb}^b$ represents the angular rate vector of the b-frame with respect to (w.r.t.) the n-frame coordinatized in the b-frame, which is what the strapped-down triad of rate gyros aligned with the b-frame axes measures. The accelerometer triad senses $f_{nb}^b$, the non-gravitational acceleration (also known as specific force) of the b-frame w.r.t. the inertial reference frame, n, expressed in b-frame.

The orientation of the b-frame w.r.t. the n-frame can be conveniently represented using a direction cosine matrix $C_b^n$, which is simply the 3×3 rotation matrix that transforms vectors from b-frame to n-frame: $v^n = C_b^n v^b$. The orientation is integrated, starting from a known initial orientation matrix, using the differential equation.

$$\dot{C}_b^n = C_b^n S(\omega_{nb}^b), \quad (1)$$

where $S(\omega_{nb}^b) \equiv [\omega_{nb}^b \times]$ is the skew-symmetric matrix formed from the elements of $\omega_{nb}^b$ to implement the cross-product operator noted in the square brackets. The updated rotation matrix is then used to resolve the accelerometer readings into the n-frame, whence they can be easily corrected for the effect of gravity and double integrated to obtain the head position using:

$$\dot{v}_{nb}^n = C_b^n f_{nb}^b + g^n \quad (2)$$

$$\dot{r}_{nb}^n = v_{nb}^n$$

where $g^n \approx [0\ 0\ 9.8\ m/s^2]^T$ is the local apparent gravity vector which by definition points downward in navigation (nav) frame, and the derivatives are both calculated relative to nav frame.

Equations (1) and (2) are integrated numerically in the InterSense IS-600 processor to keep track of orientation, velocity and position. They may appear overly simple, but the gyro sensors in the InterSense InertiaCube™ IMU are not sensitive enough to detect the 15°/hr rotation of the earth, so there is no need to include terms to compensate for its effect on the sensors. The drift that results from using such low-performance gyros and neglecting the effects of earth rotation must be frequently corrected by other means, ultrasonic position sensors and a drift correction Extended Kalman Filter in the case of the IS-600.

1.2 Inertial Tracking Relative to Rotating Earth

In this section, we review the basic equations of terrestrial navigation, primarily as a source of inspiration for the derivation in the following section, which deals with a similar problem of tracking a moving body relative to another moving body.

Figure 2:
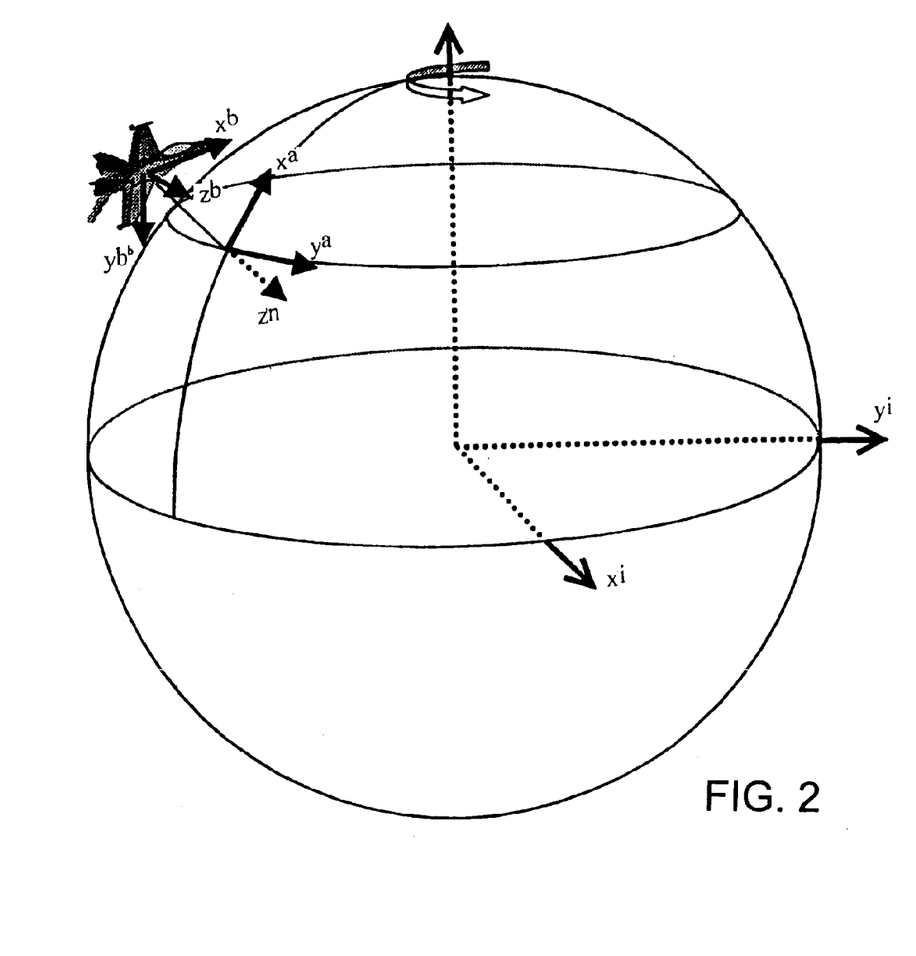
FIG. 2 shows inertial navigation relative to rotating earth.

Unlike the previous section, we will now need three coordinate frames. The inertial frame, or i-frame, has its origin at the center of the earth, but its axes do not rotate with the earth, rather they stay fixed with respect to the distant stars. The orbit of this frame about the sun is so slow that it is perfectly adequate to treat it as an inertial reference frame. Just as before, the body frame is defined fixed in the body being tracked, now an airplane, with the x-axis forward, y-axis right, and z-axis down. The navigation frame (n-frame) is now defined as a locally-level frame with its x,y,z-axes aligned to the local north, east and down directions respectively, as shown in FIG. 2. The down direction is defined by the local apparent gravity vector $g_l$, the direction a plumb bob hangs, which is the resultant vector of the mass attraction vector towards the earth and the centrifugal acceleration vector away from the earth rotation axis felt by an object stationary on the ground.

In real-life terrestrial navigation, the n-frame follows the aircraft around, having its origin always at the current aircraft position. Therefore, position and velocity cannot be specified with respect to n-frame, and it is necessary to introduce yet another frame, called e-frame, with its axes fixed in the earth. The usual strategy for aircraft navigation is to calculate the "groundspeed" $v_e$ relative to the earth, but coordinatize it in n-frame. This is convenient because 1) it is much easier to compute local gravity in n-frame, and 2) the north, east, and down velocities can be directly integrated to keep track of position in terms of latitude, longitude and altitude, which are the desired coordinates for global navigation. However, for the present purposes, this adds some extra terms that are not needed for the derivation in the next section. For simplicity we will simply "freeze" the n-frame at a particular point on the earth, and assume that the plane flies around staying close enough to the origin of the n-frame that we can neglect curvature of the earth over this flying range.

We wish to track the airplane relative to the n-frame, which itself is moving relative to the inertial reference frame. The inertial measurement unit (IMU) on the airplane always measures the angular velocity and non-gravitational acceleration of the airplane relative to inertial space, expressed in b-frame: $\omega_{ib}^b$ and $f_{ib}^b$. Since $\omega_{ib} = \omega_{in} + \omega_{nb}$, we have $$\omega_{nb}^b = \omega_{ib}^b - C_n^b \omega_{in}^n, \quad (3)$$

which can be substituted into equation (1) and integrated to track the current orientation. $\omega_{ib}^b$ is available directly from the gyros, and $\omega_{in}{}^n$ can be calculated based on earth's rate and the latitude L. In the next section, where the n-frame is moving somewhat less predictably than the earth's rotation, $\omega_{in}{}^n$ cannot be calculated, but it can be directly measured by gyros mounted on the moving platform.

To find the aircraft's velocity and position relative to the n-frame, which is rotating relative to the inertial frame, we need to make use of the Law of Coriolis, which can be stated in it's most general form as $$D_a = D_b + \omega_{ab} \times \tag{4}$$

where $D_a$ represents an operator that differentiates any vector w.r.t. the a-frame, and a and b are any two Cartesian coordinate frames that share a common origin but are rotating with a relative angular velocity $\omega_{nb}$. Start with the equations of motion in the inertial frame, which are exceptionally straightforward:

$$D_i^2 r_{ib} = f_{ib} + g_m \tag{5}$$

This is a vector relationship, which will hold true in any coordinate frame, thus the lack of superscripts. $g_m$ represents a pure mass attraction gravity vector. We now wish to convert this into n-frame. Expanding the left side of equation (5) with the Coriolis operator (4) we get:

$$\begin{aligned} D_i^2 r_{ib} &= \{D_i^2 r_{in}\} + \{D_i^2 r_{nb}\} \\ &= \{(D_n + \omega_{in} \times)^2 r_{in}\} + \{(D_n + \omega_{in} \times)^2 r_{nb}\} \\ &= \{(D_n + \omega_{in} \times)(D_n r_{in} + \omega_{in} \times r_{in})\} + \\ &\quad \{(D_n + \omega_{in} \times)(D_n r_{nb} + \omega_{in} \times r_{nb})\} \\ &= \{(D_n r_{in} \times r_{in} + \omega_{in} \times D_n r_{in} + \omega_{in} \times (\omega_{in} \times r_{in})\} + \\ &\quad \{D_n^2 r_{nb} + D_n \omega \times r_{nb} + \omega_{in} \times D_n r_{nb} + \omega_{in} \times D_n r_{nb} + \\ &\quad \omega_{in} \times (\omega_{in} \times r_{nb})\} \\ &= D_n^2 r_{nb} + 2(\omega_{in} \times D_n r_{nb}) + \omega_{in} \times (\omega_{in} \times (r_{in} + r_{nb})) \\ &= \dot{v}_{nb} + 2(\omega_{in} \times v_{nb}) + \omega_{in} \times (\omega_{in} \times r_{ib}) \end{aligned} \tag{6}$$

where terms containing $D_n \omega_{in}$ or $D_n r_{in}$ are dropped because $\omega_{in}$ and $r_{in}$ are constant vectors in the n-frame. Equating this to the right side of equation (5), we have $$\begin{aligned} \dot{v}_{nb} &= f_{ib} + g_m - \omega_{in} \times (\omega_{in} \times r_{ib}) - 2(\omega_{in} \times v_{nb}) \\ &= f_{ib} + g_l - 2(\omega_{in} \times v_{nb}) \end{aligned} \tag{7}$$

where $g_l \equiv g_m - \omega_{in} \times (\omega_{in} \times r_{ib})$ is the local apparent gravity caused by both mass attraction and centrifugal acceleration acting on the body due to earth's rotation. Gathering the results in one place, the navigation equations are:

$$\dot{C}_b{}^n = C_b{}^n S(\omega_{ib}{}^b - C_n{}^b \omega_{in}{}^n)$$

$$\dot{v}_{nb}{}^n = C_b{}^n f_{ib}{}^b + g_l{}^n - 2(\omega_{in}{}^n \times v_{nb}{}^n) \tag{8}$$

$$\dot{r}_{nb}{}^n = v_{nb}{}^n$$

which may readily be integrated using the inputs $\omega_{ib}{}^b$ and $f_{ib}{}^b$ from the aircraft IMU, plus the quantity $\omega_{in}{}^n$ which is calculated from earth rotation rate and the known latitude of the n-frame origin. Comparing to equations (1) and (2), these differ only by the addition of some extra terms to compensate for the effect of the rotation rate of the n-frame, $\omega_{in}{}^n$, on the gyros and accelerometers. These extra terms are tiny or slowly varying compared to the original terms. It is therefore traditional to integrate these terms at a rate much lower than the numerical integration rate of the larger terms, which is typically several hundred Hz.

1.3 Inertial Tracking Relative to an Arbitrary Maneuvering Platform

We track a person's head relative to a maneuvering platform by borrowing the mathematics that an inertial navigation system uses to track an airplane relative to a rotating earth, as outlined in the previous section. Some modifications will be required because the platform motion is more dynamic and unpredictable than the earth's rotation:

1) We cannot simply calculate $\omega_{in}{}^n$ based on the known constant earth rotation and latitude. Instead, we will have to attach a reference IMU to the platform and use its gyros to measure $\omega_{in}{}^n$.
2) We cannot use the $D_n \omega_{in}$ or $D_n r_{in} = 0$ simplifications.
3) Unlike the earth, the platform may be accelerating as well as rotating, so we must add terms to the navigation equation based on the reference IMU accelerometer readings.
4) Platform motion cannot be assumed slow, so all the terms must be included in the m-rate integration algorithms.
5) The motion platform is maneuvering unpredictably, and is no longer a locally-level reference frame. The apparent gravity vector does not always point straight down in the platform frame.

In light of these complications, one approach would be to use a locally level n-frame attached to the ground, and use the ground-relative tracking algorithm of section 1.1 to track both the motion platform (p) and the user's head (h) relative to the ground (n). Then the user's head pose relative to the motion platform can be computed using $C_h{}^p = C_n{}^p C_h{}^n$ and $r_{p \to h}{}^p = C_n{}^p (r_{n \to h}{}^n - r_{n \to p}{}^n)$.

Figure 3A:
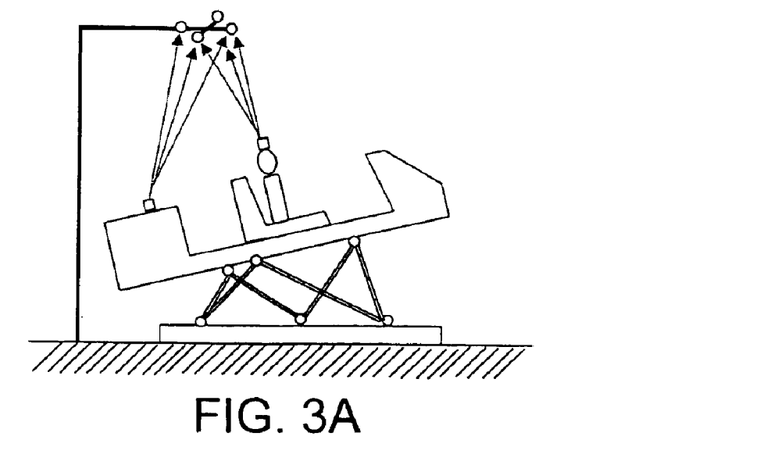
FIG. 3a shows tracking a platform and head relative to ground, using inertial and ground-relative absolute sensors.
Figure 3B:
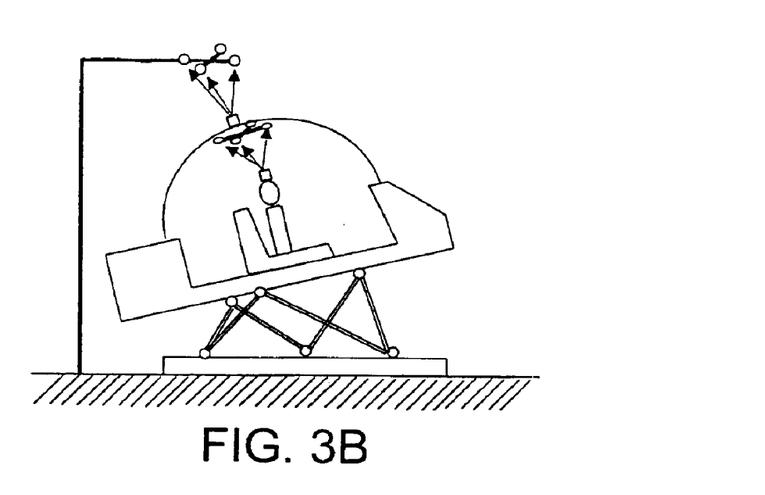
FIG. 3b shows tracking a platform relative to ground, and a had relative to ground (inertial) aided by platform-mounted sensors with known position relative to ground

Several engineers familiar with the operation of the IS-600 have suggested this approach. However, in many practical situations, there is a problem. The IS-600 normal tracking algorithm described in section 1.1 requires a clear acoustical path between the tracked object and the receiver X-bar for making the drift-correcting range measurements. This is fine for open-top motion-base simulators that are sometimes used with HMD-based systems, as illustrated in FIG. 3a. However, many motion-base simulators have closed-top simulator cabs, which would effectively prevent the use of acoustic, optical, or magnetic devices for providing auxiliary measurements of the head position relative to a receiver unit mounted at a fixed location outside the simulator cab. A possible solution to this problem is illustrated in FIG. 3b. Here again, both the head and platform inertial systems track relative to the ground, using the algorithms of Section 1.1. For the platform-tracker, the drift-correcting range measurements are made relative to an external X-bar fixed in the environment, as usual. For the head-tracker, aiding measurements relative to the ground are required to correct the inertial measurements, but the X-bar visible to the head-tracker is mounted on the moving simulator platform. To create virtual measurements relative to the ground, we could use the known simulator platform pose to transform the positions of the X-bar receiver pods into the fixed reference frame before processing their range measurements. In some cases, the external X-bar could be eliminated by utilizing data from encoders on the motion base actuators if they were available and could offer millimeter precision in real-time.

Figure 3C:
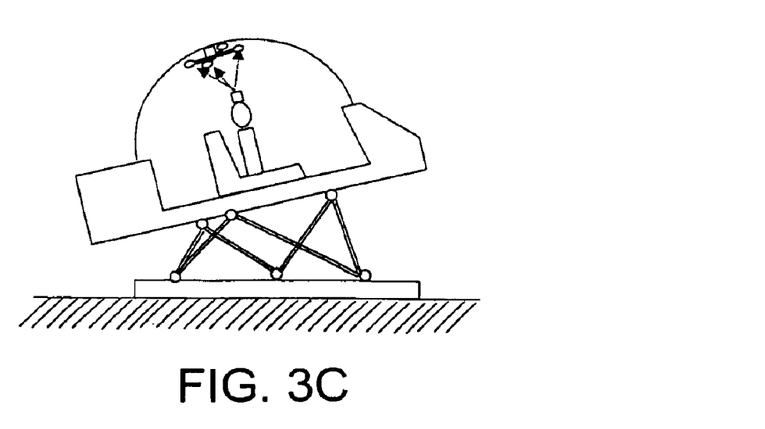
FIG. 3c shows tracking a head relative to a platform, using a self-contained system.

This may be a viable approach for some simulators, but it won't work for tracking on moving vehicles, where millimeter-level vehicle position data is generally not available. In vehicular tracking applications (and most simulators too), all that is required is the head pose relative to the moving platform. It would be desirable to find a method of measuring this pose directly, without having to track the vehicle with respect to the ground as well and to compute the pose difference afterwards. This would result in a general-purpose tracking system that would work with any type of moving platform, and the installation would be simpler because the whole system would be installed on the inside. FIG. 3c illustrates the hardware for such a system, installed in a motion-base simulator cab. In the remainder of this section, an approach is developed for doing this.

Figure 3D:
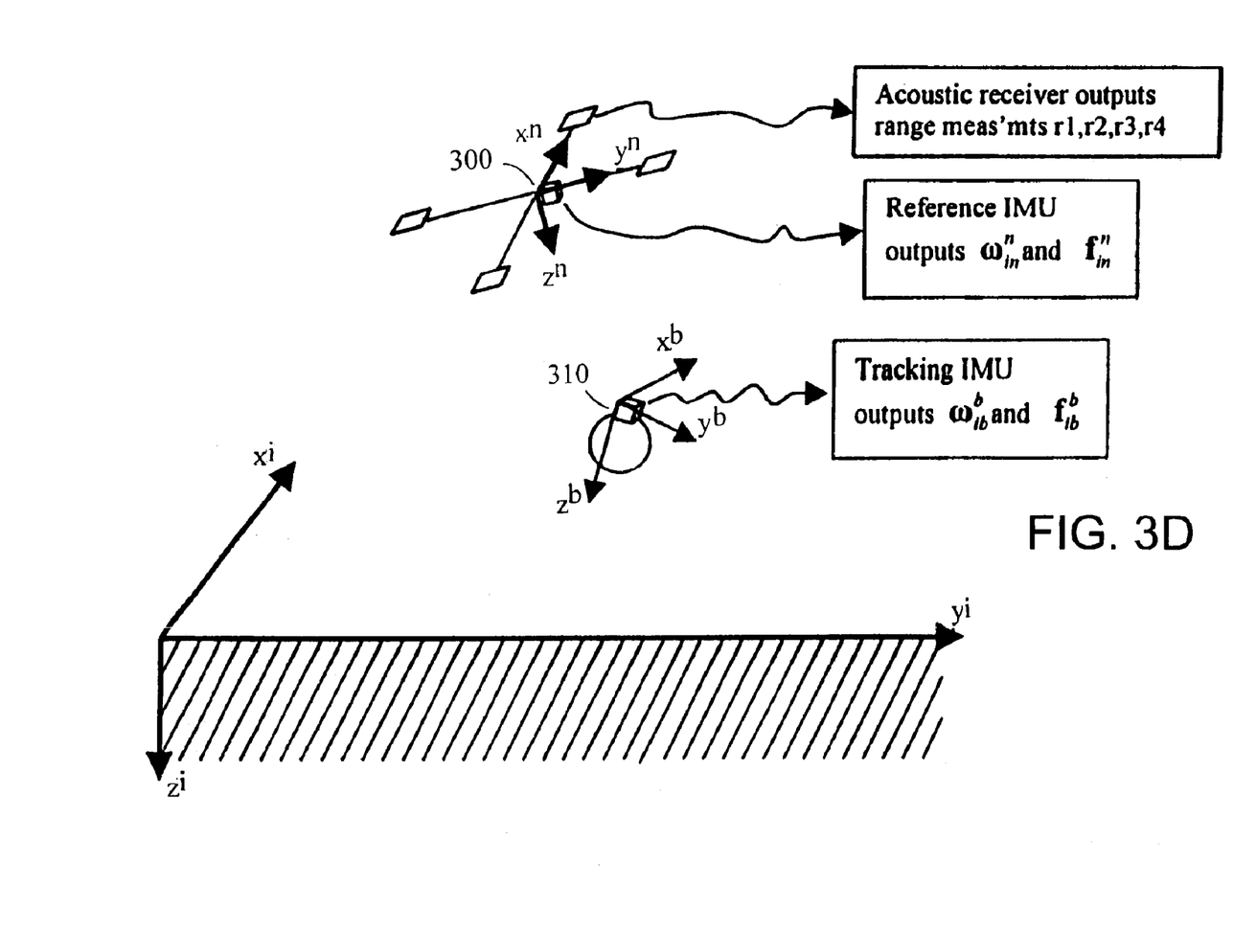
FIG. 3d shows coordinate system conventions for the relative tracking system of FIG. 3c.

The first step to achieving the desirable tracking system illustrated in FIG. 3c is to choose the navigation frame fixed to the moving platform. FIG. 3d illustrates a particularly convenient choice of n-frame axes, centered at the reference IMU 300 and aligned with its axes. The reference IMU 300 is bolted to the center of an IS-600 X-bar (or any other reference tracking device), which in turn is bolted to the canopy of the simulator cab or cockpit. This may seem somewhat strange to those accustomed to inertial navigation systems, where the n-frame is always a locally-level frame with its vertical axis aligned with the direction of local gravity. The main purpose of the n-frame in fact is to provide a digital equivalent to an old-fashioned mechanically-gimbaled inertial navigation system (INS), in which gyros on the gimbals are used to servo-stabilize an accelerometer triad into a level and north-slaved attitude, even as the vehicle maneuvers about. With the accelerometers always held in this North-East-Down orientation, one need merely add 1 g to the output of the z accelerometer, then double integrate the accelerometer outputs to track position in the nav frame. In strapdown systems, the stored $C_b^n$ matrix is used to transform the accelerometer readings into nav-frame, then do exactly the same thing, as described in equation (2). To use this technique with the dancing n-frame illustrated in FIG. 3d, it may seem necessary to constantly keep track of $C_n^i$ (just what we are trying to avoid doing) in order to figure out the effect of local gravity in the n-frame and compensate for it. However, in one aspect of the invention, we provide an alternative.

We can use the reference IMU to measure the gravitational field in the n-frame at every time step, instead of trying to calculate it? The key that makes this approach possible is the realization that it is not necessary to explicitly compensate for the effect of earth's gravitation on the b-frame accelerometers. It is the combined effect of gravity and acceleration of the n-frame that disturbs the b-frame accelerometers and must be removed before integration. It happens that this summed effect is exactly what the reference IMU accelerometers measure. Using this observation to our advantage, we now repeat the derivation of Section 1.2, but without the luxury of canceling any terms due to constancy of n-frame rotation. Starting again with the universal i-frame equation of motion (5), we proceed in similar manner to equation (6), except we don't expand the $D_i^2 r_{in}$ term:

$$D_i^2 r_{ib} = D_i^2 r_{in} + \{D_i^2 r_{nb}\} \quad (9)$$

$$= D_i^2 r_{in} + \{(D_n + \omega_{in} \times)^2 r_{nb}\}$$

$$= D_i^2 r_{in} + \{(D_n + \omega_{in} \times)(D_n r_{nb} + \omega_{in} \times r_{nb})\}$$

$$= D_i^2 r_{in} + \{D_n^2 r_{nb} + D_n \omega_{in} \times r_{nb} + \omega_{in} \times D_n r_{nb} +$$

-continued
$$\omega_{in} \times D_n r_{nb} + \omega_{in} \times (\omega_{in} \times r_{nb})\}$$

$$= D_i^2 r_{in} + \dot{v}_{nb} + \dot{\omega}_{in} \times r_{nb} + 2(\omega_{in} \times v_{nb}) + \omega_{in} \times (\omega_{in} \times r_{nb})$$

Using equation (5) to substitute both $D_i^2 r_{ib} = f_{ib} + g_m$ and $D_i^2 r_{in} = f_{in} + g_m$ and rearranging terms, we get $$\dot{v}_{nb}^n = C_b^n f_{ib}^b - \dot{\omega}_{in}^n \times r_{nb}^n - 2(\omega_{in}^n \times v_{nb}^n) - \omega_{in}^n \times (\omega_{in}^n \times r_{nb}^n) - f_{in}^n \quad (10)$$

where the orientation matrix $C_b^n$ comes from integrating $$\dot{C}_b^n = C_b^n S(\omega_{ib}^b - C_n^b \omega_{in}^n) \quad (11)$$

and position $r_{nb}^n$ is obtained by integrating $$\dot{r}_{nb}^n = v_{nb}^n \quad (12)$$

just as in Section 1.2.

If the reference IMU is mounted at the origin of the n-frame, then it directly measures $f_{in}^n$ and $\omega_{in}^n$, so (10) is the complete navigation equation, which can be integrated using just data available from the two IMUs. (A numerical approximation to the derivative of $\omega_{in}^n$ is needed if angular accelerometers are not available on the reference IMU.) The second, third and fourth terms are new additions compared to the stationary platform equation (2). They represent tangential, Coriolis, and centripetal accelerations respectively which result from the rotation of the n-frame. The Coriolis and centripetal terms are also present in the rotating earth navigation equation (8), with the latter being absorbed inside the definition of local gravity. The tangential acceleration term requires noise-boosting numerical differentiation of the discrete-time gyro outputs, and so could be a potential source of significant integration error if the lever arm $r_{nb}^n$ from the reference IMU to the tracking IMU 310 is too long.

The fifth term, $-f_{in}^n$, replaces $g_l^n$, and incorporates both the effect of $g_m^i = [0\ 0\ g]^T$ rotated into the tilted n-frame as well as actual acceleration of the platform. By measuring the effect of gravity directly in the n-frame with a reference IMU, we do not need to know the platform tilt angles to resolve the gravity vector into the n-frame. Thus, this system operates independently without any inputs from the motion-base controller or the vehicle attitude reference system, and without the need to ever know or measure or calculate the orientation or position of the moving platform.

If the reference IMU is located at a non-zero offset position $r_{RIMU}^n$ from the n-frame origin, then it will measure $$\tilde{f}_{in}^n = f_{in}^n + D_i^2 r_{RIMU}^n \quad (13)$$

$$= f_{in}^n + \dot{\omega}_{in}^n \times r_{RIMU}^n + \omega_{in}^n \times (\omega_{in}^n \times r_{RIMU}^n)$$

Therefore, we must first remove the effects of tangential and centripetal acceleration from $\tilde{f}_{in}^n$:

$$f_{in}^n = \tilde{f}_{in}^n - \dot{\omega}_{in}^n \times r_{RIMU}^n - \omega_{in}^n \times (\omega_{in}^n \times r_{RIMU}^n)$$

then pass this true $f_{in}^n$ into the navigation equation (10). This may add additional computation and numerical errors, which could be avoided by defining the n-frame origin at the reference IMU (as shown in FIG. 3d) and then subtract $r_{RIMU}^n$ from the final computed result $r_{nb}^n$.

2 Simulation Results 2.1 IS-600 MPT Configuration Description

As an example of an implementation approach, we now define a specific tracking system configuration called IS-600

Figure 4:
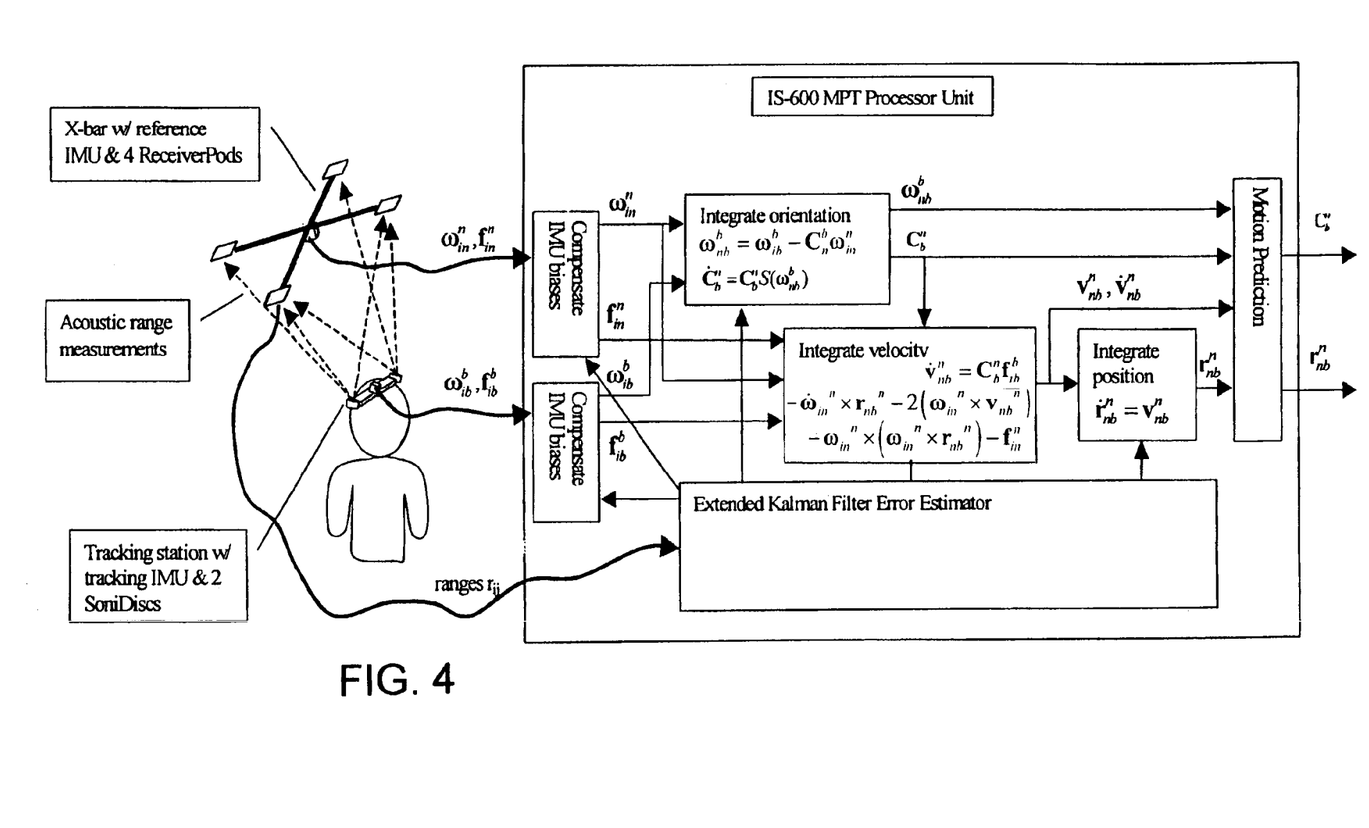
FIG. 4 shows an IS-600 MPT configuration and block diagram.

MPT. Referring to FIG. 4, the IS-600 MPT is a derivative of the InterSense IS-600 Mark 2 motion tracking system. Like the IS-600M2, the MPT has a reference X-bar 400 which holds four ultrasonic receiver pods 410, a tracking "station" 420 consisting of the tracking IMU 430 and two SoniDisc ultrasonic beacons 440 rigidly mounted on a strip about 6 inches long, and a rack-mount processor unit 450. The processor unit gathers the data from the various sensors, performs integration and sensor fusion algorithms, and outputs the cooked 6-DOF data to a host by serial port. The processor unit includes bias compensation units 465, an orientation integration unit 470 for integrating the orientation values, a velocity integration unit 475 for integrating velocity values, a position integration unit 480 for integrating position values. All of these units receive correction values generated by the extended Kalman filter error estimator unit 485. The values generated by these units are fed into the motion prediction unit 490, which generates predicted motion values. In addition, the IS-600 MPT has an additional reference IMU 460 mounted at the center of the X-bar where the default origin for the tracking reference frame (n-frame) is located. FIG. 4 illustrates the IS-600 MPT configuration as simulated in Section 2.3, including the enhanced kinematic integration algorithm derived in Section 1.3 for inertial tracking relative to a moving platform.

2.2 Bias Observability Problem

A careful examination of FIG. 4 reveals a potential problem with the proposed relative inertial tracking approach. One of the important tasks of the Extended Kalman Filter (EKF) error estimator is to estimate the inertial sensor biases, so that this information can be used to compensate the IMUs before performing the numerical integration of kinematics equations (11), (10), and (12). It is known that, for the case of fixed platform tracking using a single IMU, the complementary EKF formulation can successfully estimate and compensate for gyro biases. It is able to do this by indirectly observing the effect of the gyro biases on the propagation of orientation errors over time. Since a gyro bias on a particular gyro will cause orientation error to accumulate in a particular way, the filter can unequivocally trace back the orientation error to the offending gyro and correct its bias.

For the relative inertial tracking system of FIG. 4, there are actually 6 gyros contributing to the integration of the 3-DOF orientation through equation (11). For any particular orientation of the b-frame relative to n-frame, any number of gyro bias combinations might result in the same orientation drift pattern. For example, when the relative yaw, pitch and roll between the platform and the head are all zero, $C_n^b = I^{3 \times 3}$, and $\omega_{nb}^b = \omega_{ib}^b - \omega_{in}^n$. Equal gyro biases on the x-gyros of both IMUs would therefore cause the n-frame and b-frame to both rotate in the same direction so that the relative orientation would not change. Therefore, these nonzero gyro biases would be unobservable by a state estimator (EKF) that only receives measurements of the relative orientation of the two frames. Due to space limitations, we will not calculate the observability Grammian to prove this, but rather accept it intuitively. A similar problem exists for accelerometer bias observability while the two frames are in any particular fixed pose relative to one another.

Fortunately, it also seems intuitively reasonable that the observability problem will disappear as long as the b-frame is moving relative to the n-frame. Consider starting at the [0 0 0] relative orientation holding steady. After a moment, the state estimator will not know any of the individual gyro biases specifically, but it will know that the difference between the two x gyro biases is a certain value. Now suppose the b-frame suddenly rotates to yaw angle 90° relative to the n-frame. Now the tracking x-gyro is paired with the reference y-gyro and vice versa and the x and y-gyro biases of both IMUs will become observable. After another rotation about a different axis, the z-gyros will become observable as well. Therefore, it would seem that the tracker should still work as long as the user occasionally moves her head. Whether this is acceptable or not depends on how frequently she must move her head in order to keep the tracking system performing within specifications. If the tracker only starts to degrade noticeably in performance half an hour after the user stops moving completely, this is unlikely to be a problem for most real applications. In the next section, a simulation is developed and used to experiment with the effect of user motion or lack thereof on tracking quality.

2.3 Simulation Results

A simulation has been written to evaluate the performance of the proposed algorithm, and the seriousness of the bias observability problem just described. The inputs to the simulation are two "truth" trajectory files, one describing the motion of the platform ($C_n^i(t)$ and $r_{in}^i(t)$), and the other describing the motion of the head relative to the platform ($C_b^n(t)$ and $r_{nb}^n(t)$). The simulation performs the following steps:

1) Calculates the "truth" motion of the head relative to i-frame from the two input files.
2) Calculates ideal reference IMU outputs $f_{in}^n$ and $\omega_{in}^n$ from the platform trajectory.
3) Calculates the ideal tracking IMU outputs $f_{ib}^b$ and $\omega_{ib}^b$ from the i-frame head motion found in step 1.
4) Corrupts both IMU outputs with realistic levels of noise and bias error, representative of InertiaCube performance.
5) Feeds these simulated IMU outputs, as well as simulated range measurements (also corrupted with an appropriate level of noise) through the IS-600 MPT processor algorithms as depicted in FIG. 4.
6) Plots the tracking system errors (the difference between the trajectory calculated by the simulated IS-600 MPT processor and the "truth" trajectory), together with the 1-sigma covariance bounds calculated by the EKF.

Figure 5:
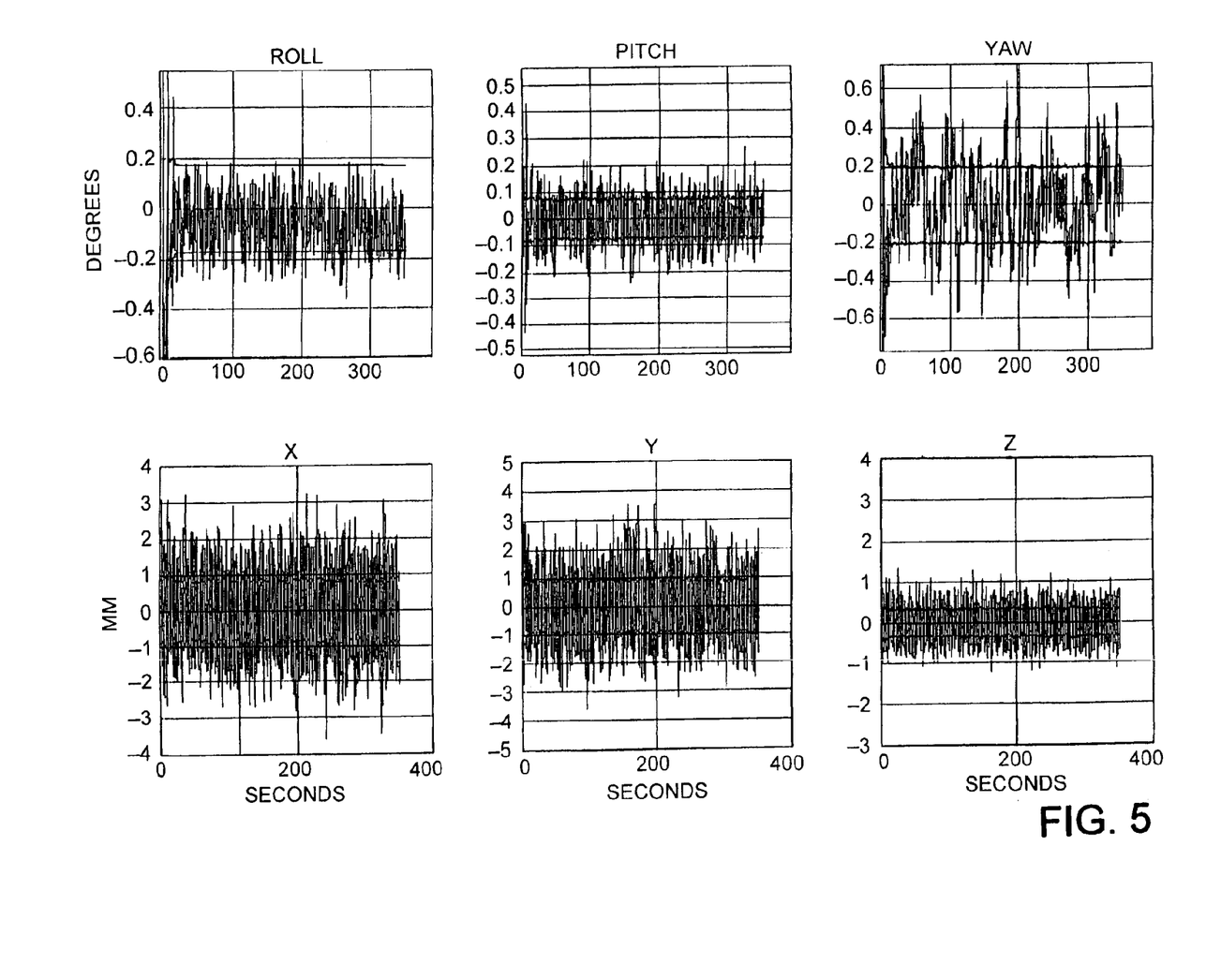
FIG. 5 shows simulated tracking errors and 1-sigma covariance bounds for a 6-minute run.

FIG. 5 shows the tracking system pose estimation errors (roll, pitch, yaw, x, y, and z errors) for a 6-minute run, simulated with a 30 Hz update rate. The platform trajectory had no motion. The head w.r.t. platform trajectory had a 30° yaw rotation (head shake) followed by a 30° pitch rotation (head nod) 10 seconds after the beginning of the simulation, and no motion thereafter. The tracking performance, approximately 0.2° rms in orientation and 1 mm rms in position, is only slightly degraded from an ordinary fixed platform IS-600 simulation with the same X-bar configuration and update rate. The interesting thing is that after the initial shake and nod, which were included to "get a fix" on the biases, the tracking continues for another 5½ minutes with no motion at all, and no noticeable increase in position or orientation errors.

Figure 6:
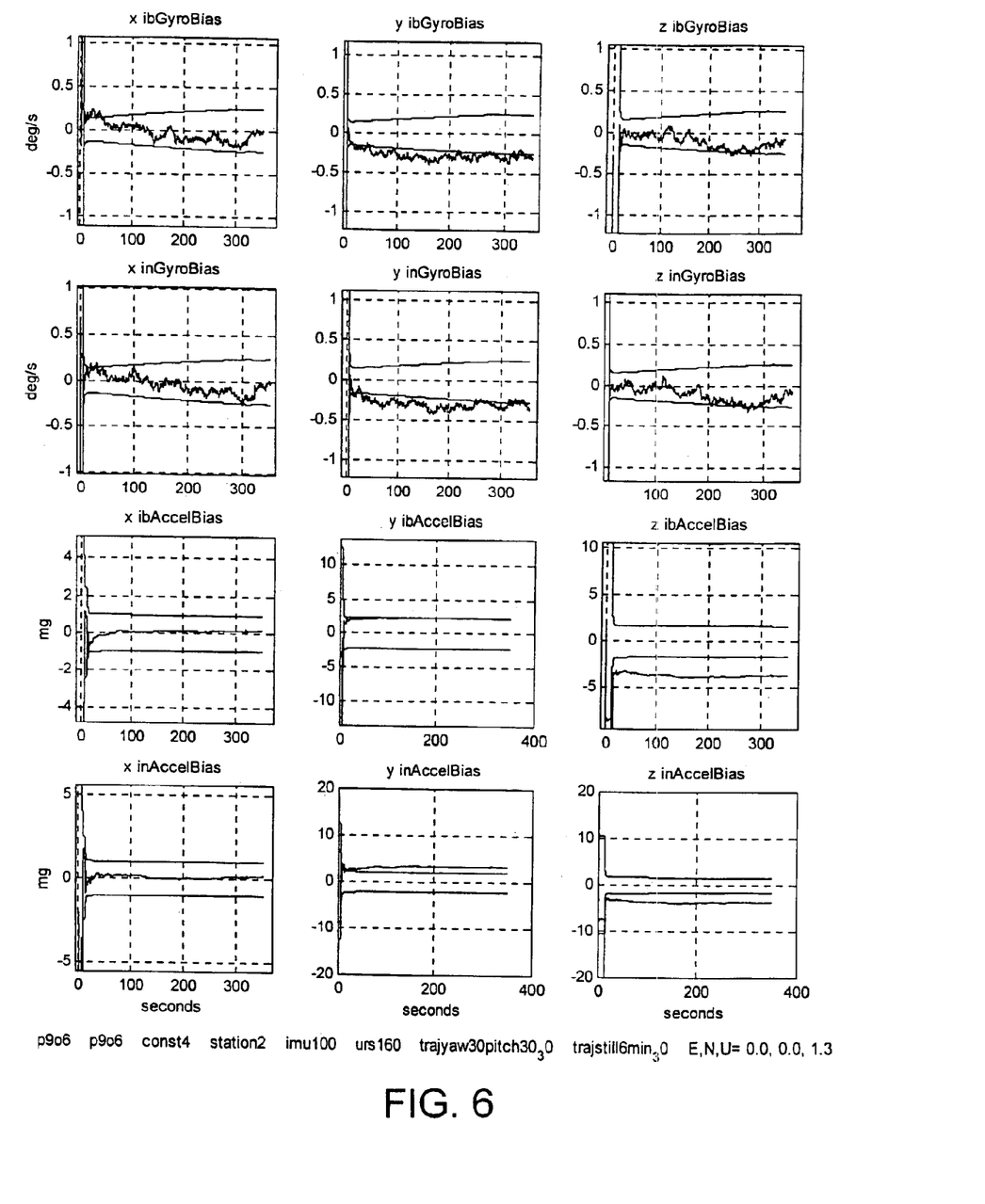
FIG. 6 shows simulated IMU bias estimation errors and 1-sigma covariance bounds for a 6-minute run.

FIG. 6 shows what happens to the bias estimation errors. As in FIG. 5, the differences between the filter-estimated biases and the actual biases that were used to corrupt the ideal IMU outputs are plotted, together with the filter-calculated 1-sigma covariance bounds on the bias states. If you zoom in on the beginning section of the graphs, you can see that initially the bias covariances stay approximately where they were initially set, because they are not yet observable. After the yaw rotation, the x and y gyro biases for both IMUs rapidly come down to normal operating levels. After the pitch rotation, the z biases also come down, all as we would expect from the observability discussion in Section 2.2. Over the remaining 5½ minutes, we see the gyro bias error covariances gradually climbing back upwards due to lack of observability during the motionless period. Interestingly, the increasing bias errors do not seem to have any significant effect on the pose estimation errors over this time period. It also appears that the accelerometer biases do not increase noticeably.

Another simulation run was performed to see how long good-quality tracking can be sustained with no user head-motion. Again, the head-motion trajectory began with a 30° shake/nod to set the biases, but then was followed by a half-hour of stillness, this time sampled at 5 Hz to keep the file sizes manageable. The same pattern emerged. The gyro biases (but not accelerometer biases) gradually crept up from the level they had been set to after the initial wiggle. By the end of a half-hour they had reached 0.5°/s, but still with no noticeable increase in the pose estimation error covariances. At that point, the trajectory contained a second wiggle, but this time only 10° in amplitude. This small wiggle of the head was sufficient to send the biases back down to 0.3°/s. From this it seems likely that the tracking will work fine as long as the user wiggles his head by at least 10° at least every half-hour. There is little point tracking a person's head if he is dead, so we don't consider this a very limiting requirement. Additional simulation runs have been performed which included motion of the platform, to confirm that the kinematic algorithms really work to extract only the relative motion. Indeed it was found that the errors in the relative tracking of the head w.r.t. the platform only increase slightly when the platform is flying tight figure-8's. This confirms that the relative navigation equations derived in Section 1.3 are correct, and that the Kalman filter model developed around them is working. We have described a new approach to head-tracking on moving vehicles or motion-base simulator platforms, based on differential inertial sensing. This approach allows the benefits of inertially-based motion tracking to be realized on moving platforms, without the head-tracking accuracy being disturbed by the unpredictable motions of the platform. One feature of the described method is that it is self-contained: the tracking system does not need to be provided with any external information about the platform motion, and it can be installed locally inside the volume being tracked, just like an ordinary fixed-base tracking system.

Although the results have been illustrated using an acoustic/inertial hybrid tracking system configuration based on the InterSense IS-600, the basic concept is equally applicable with any other type of aiding measurements for the inertial sensors, including the magnetic or optical tracking systems that are currently used in many cockpit helmet-tracking applications.

An optical/inertial hybrid helmet-tracking system, to be designated as the IS-1200 FlightTracker, has recently been developed.

Figure 7:
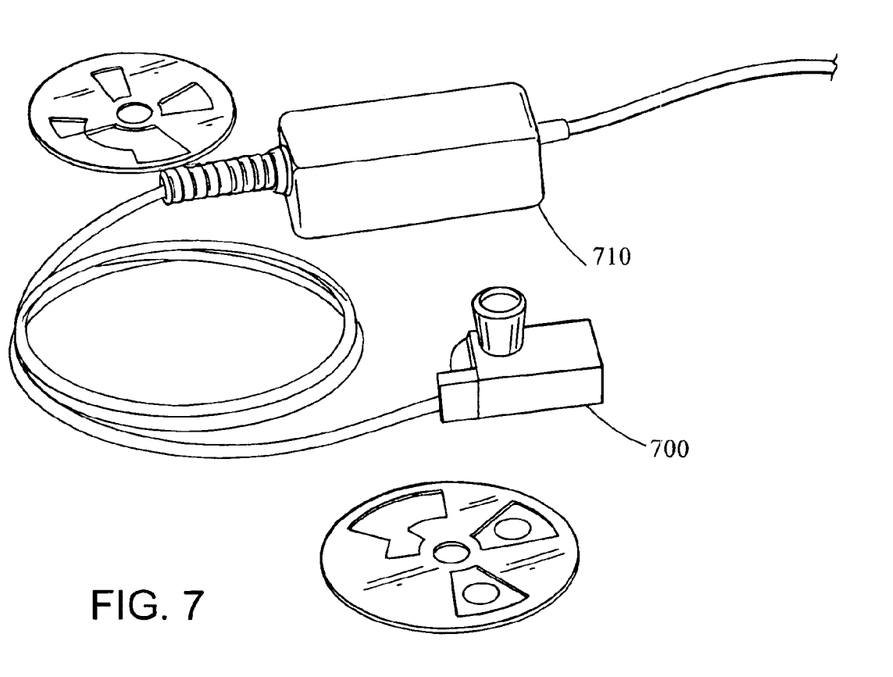
FIG. 7 shows an integrated inertial/optical sensor unit.

The IS-1200 is a modular product line based on combining data from one or more "InertiaCam™" integrated inertial/optical sensor units. FIG. 7 shows an illustration of an InertiaCam, which consists of a miniature sensor head 700 and an electronics unit 710. The sensor head contains three MEMS gyroscopes, 3 MEMS accelerometers, a CCD video sensor, and a lens. The electronics unit contains interface electronics and a DSP programmed with firmware for performing all the necessary image processing operations to extract the relevant targets from the CCD image and determine their locations with sub-pixel accuracy. The InertiaCam has image processing algorithms capable of extracting either passive visible targets (such as the circular barcodes shown in the photograph) or active targets (such as IR LEDs, visible LEDs, ultraviolet LEDs, or retroreflective markers).

The IS-1200 system also includes a base unit or computer, which receives data from one or more sensing devices through its sensor ports, and fuses the data using flexible sensor fusion software as described in pending U.S. patent application Ser. No. 10/639,242, which is incorporated herein by reference.

Figure 8:
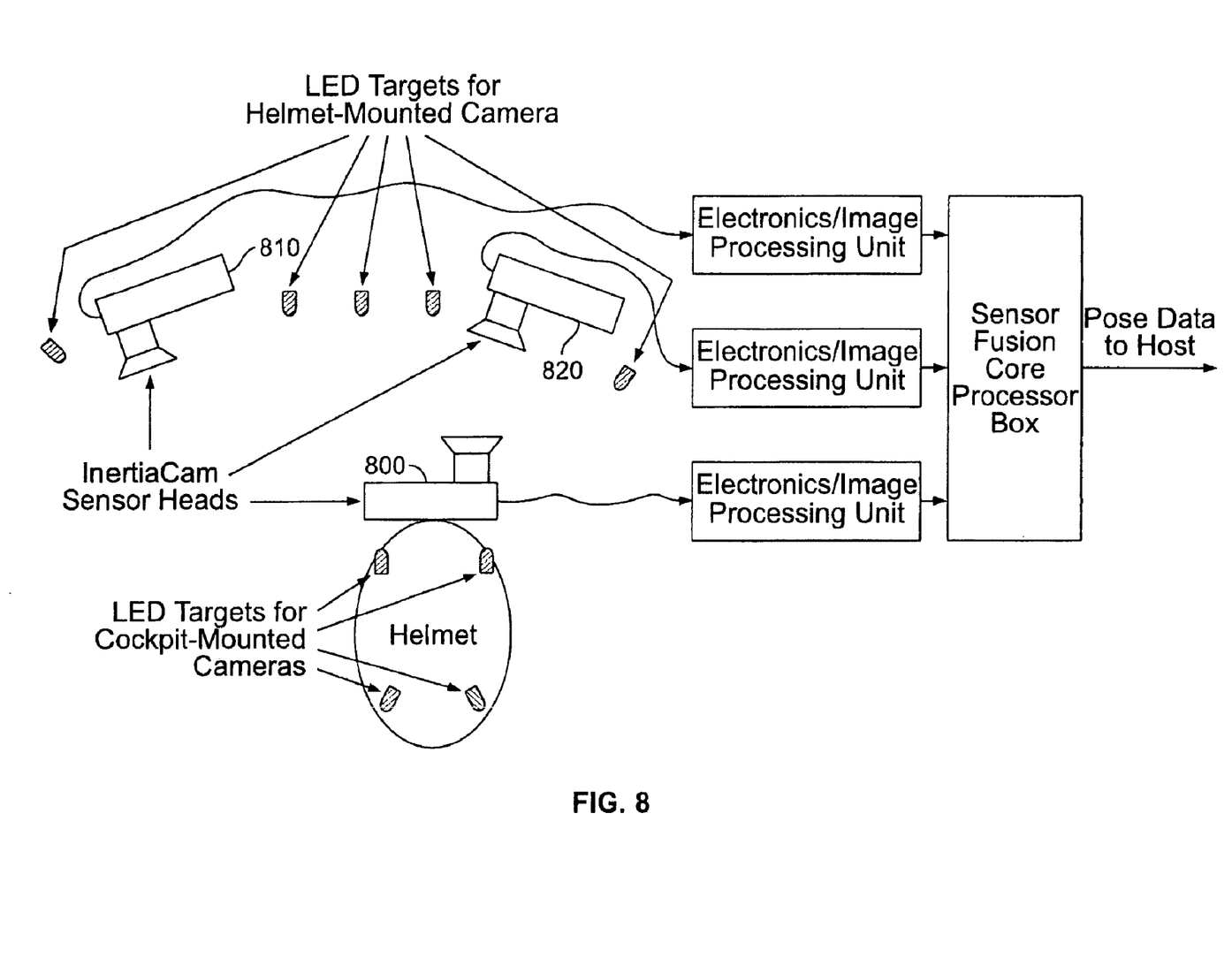
FIG. 8 shows a schematic diagram of an embodiment of the invention.

FIG. 8 shows a schematic diagram of the IS-1200 Flight-Tracker system. The system employs three InertiaCams 800, 810, and 820. One (800) has its sensor mounted on the pilot's helmet; the other two InertiaCam sensors (810, 820) are mounted at fixed points in the cockpit, for example on the sides of the canopy bow or instrument panel. The inertial sensors contained in the head-mounted InertiaCam serve as the tracking IMU, and the two sets of inertial sensors in the cockpit-mounted InertiaCams together serve as the reference IMU.

There are several potential advantages of combining the data from two or more InertiaCams to form the reference IMU. Firstly, this provides redundancy in case one of them fails. Secondly, it provides some noise reduction through the effect of averaging together two noisy measurements of the cockpit inertial motion. This averaging effect may also help to attenuate any vibration modes that are not in phase at the two mounting locations. Thirdly, and most significantly, the accelerometer measurements at the two different locations in the cockpit can be combined to estimate some or all components of the cockpit angular acceleration, and this estimate may be much superior to that which can be obtained by numerically differentiating the noisy angular rate signals over time.

To illustrate how data from two spaced-apart reference IMUs can be combined to obtain improved estimates of craft angular acceleration, let us refer to the left and right cockpit-mounted InertiaCam sensors (810, 820) in FIG. 8 as $\alpha$ and $\beta$ respectively. Suppose that the displacements $r_\alpha^n$ and $r_\beta^n$ from the n-frame origin to these IMUs, and their rotations $C_\alpha^n$ and $C_\beta^n$ are known, by virtue of having mounted the devices with a precise fixture, or having measured their poses carefully after installation. During tracking, these devices make measurements, respectively, of the specific force vectors $f_{i\alpha}^\alpha$ and $f_{i\beta}^\beta$, and the angular rate vectors $\omega_{i\alpha}^\alpha$ and $\omega_{i\beta}^\beta$, all coordinatized in the frames of the IMUs making the measurements. From the measurements and the known pose parameters, we wish to calculate estimates of the n-frame angular rate, $\omega_{in}^n$, specific force, $f_{in}^n$, and angular acceleration, $\dot{\omega}_{in}^n$.

First, rotate the measurements from each reference IMU into the n-frame:

$$\omega_{i\alpha}^n = C_\alpha^n \omega_{i\alpha}^\alpha$$

$$\omega_{i\beta}^n = C_\beta^n \omega_{i\beta}^\beta \tag{14}$$

$$f_{i\alpha}^n = C_\alpha^n f_{i\alpha}^\alpha$$

$$f_{i\beta}^n = C_\beta^n f_{i\beta}^\beta \tag{15}$$

From (14) we can immediately estimate $\omega_{in}^n = (\omega_{i\alpha}^n + \omega_{i\beta}^n)/2$. Next, in order to estimate $\dot{\omega}_{in}^n$, we apply equation (13) to each reference IMU:

$$f_{i\alpha}^n = f_{in}^n + \dot{\omega}_{in}^n \times r_\alpha^n + \omega_{in}^n \times (\omega_{in}^n \times r_\alpha^n) \tag{16}$$

$$f_{i\beta}^n = f_{in}^n + \dot{\omega}_{in}^n \times r_\beta^n + \omega_{in}^n \times (\omega_{in}^n \times r_\beta^n) \tag{17}$$

Subtracting equation (16) from equation (17), we get:

$$f_{i\beta}{}^n - f_{i\alpha}{}^n = \dot\omega_{in}{}^n \times (r_\beta{}^n - r_\alpha{}^n) + \omega_{in}{}^n \times (\omega_{in}{}^n \times (r_\beta{}^n - r_\alpha{}^n)) \quad (18)$$

in which the only unknown is $\dot\omega_{in}{}^n$. If the vector $(r_\beta{}^n - r_\alpha{}^n)$ happens to lie along one of the n-frame axes (as illustrated in FIG. 8 where it lies along the y-axis pointing from left to right of the aircraft), then it is a straightforward matter to solve equation (18) to obtain the two components of $\dot\omega_{in}{}^n$ along the other two perpendicular axes. In this example, we can obtain the angular acceleration components about the x- and z-axes, corresponding to roll and azimuth angular accelerations, by measuring the difference of accelerometer readings on the right and left side of the cockpit. Unfortunately, pitch rate acceleration does not produce a difference of accelerometer readings on these two locations, so the y-component of $\dot\omega_{in}{}^n$ must still be obtained from numerical differentiation of the y-axis gyros, or by adding a single axis angular accelerometer sensor to measure this component.

Finally, by plugging the estimate of $\dot\omega_{in}{}^n$ back into equations (16) and (17) and averaging them together, we get the combined estimate of $f_{in}{}^n$:

$$f_{in}^n = \frac{f_{i\alpha}^n + f_{i\beta}^n}{2} - \dot\omega_{in}^n \times \frac{r_\alpha^n + r_\beta^n}{2} - \omega_{in}^n \times \left(\omega_{in}^n \times \frac{r_\alpha^n + r_\beta^n}{2}\right) \quad (19)$$

As the preceding discussion demonstrates, by combining the acceleration data from two reference IMUs separated by a baseline distance $r = |r_\beta - r_\alpha|$, it is possible to obtain improved estimates of two components of the angular acceleration perpendicular to the baseline vector $r_\beta - r_\alpha$. The signal-to-noise-ratio of this estimate increases with increasing baseline separation r. Assuming accelerometer noise of 1 mg, or 0.01 m/s/s, in the differential acceleration signal $f_{i\beta}{}^n - f_{i\alpha}{}^n$, and a separation of 1 meter, the noise of the estimated angular acceleration would be on the order of 0.01 rad/s/s. This is much better than that obtained by numerically differentiating a typical MEMS gyro, which might result in acceleration noise on the order of 1 rad/s/s. If the separation vector is not aligned with one of the n-frame axes, the technique may still be used to find two components perpendicular to the separation vector, combine with a third component parallel to this vector which has been obtained by either differentiation of gyro signals or from a single-axis angular accelerometer, and then rotate the three components back into the n-frame. In some applications, obtaining improved angular acceleration estimates in two axes may be sufficient. For example, the angular acceleration in the pitch axis might be so small for a certain aircraft type that it can be safely neglected in equation (10) and does not need to be measured. On the other hand, if improved angular acceleration estimates are required for all three axes, they can be obtained by adding one or more additional reference IMUs to the system, not all collinear with the α and β IMUs. For example, consider adding a third reference IMU γ such that α, β, and γ form a triangle. Now for each pair of IMUs, we get an equation of the form of (18) which provides estimates of two components of angular acceleration. To combine these six estimates along six different axes into fused estimates along the three navigation axes, consider using a least squares formulation as follows. Rewrite equation (18) in simplified matrix notation as:

$$A_{\alpha\beta}\dot\omega_{in}^n = b_{\alpha\beta} \quad (20)$$

where $A_{\alpha\beta} = -S(r_\beta{}^n - r_\alpha{}^n)$ and $b_{\alpha\beta} = f_{i\beta}{}^n - f_{i\alpha}{}^n - \omega_{in}{}^n \times (\omega_{in}{}^n \times (r_\beta{}^n - r_\alpha{}^n))$ and the notation $S(v)$ refers to the skew-symmetric matrix formed from the components of v, which implements the cross-product operator. By stacking an instance of equation (20) for each pair of IMUs, we get the stacked matrix equation $$\begin{bmatrix} A_{\alpha\beta} \\ A_{\alpha\gamma} \\ A_{\beta\gamma} \end{bmatrix} \dot\omega_{in}^n = \begin{bmatrix} b_{\alpha\beta} \\ b_{\alpha\gamma} \\ b_{\beta\gamma} \end{bmatrix} \quad (21)$$

for which the least-squares solution is $$\dot\omega_{in}^n = \left(\begin{bmatrix} A_{\alpha\beta} \\ A_{\alpha\gamma} \\ A_{\beta\gamma} \end{bmatrix}^T \begin{bmatrix} A_{\alpha\beta} \\ A_{\alpha\gamma} \\ A_{\beta\gamma} \end{bmatrix}\right)^{-1} \begin{bmatrix} A_{\alpha\beta} \\ A_{\alpha\gamma} \\ A_{\beta\gamma} \end{bmatrix}^T \begin{bmatrix} b_{\alpha\beta} \\ b_{\alpha\gamma} \\ b_{\beta\gamma} \end{bmatrix} \quad (22)$$

This solution blends information from all three IMUs to provide estimates of all components of the angular acceleration vector.

These methods of estimating angular accelerations from multiple separated accelerometers may be used in systems with acoustic, optical, RF, magnetic, mechanical or any other method of inertial tracker drift correction. The optical system illustrated in the above embodiment is one example of optical aiding, in which measurements made by a head-mounted camera are combined with measurements from two cockpit-fixed cameras to obtain especially high robustness. However, the system can also be operated using only one or more head-mounted cameras (in which case at least one reference IMU fixed to the vehicle should also be provided for compensation of the vehicle motion), or using only cockpit-mounted cameras (in which case a simple IMU instead of the combined IMU/camera unit is used on the helmet or tracked object).

The InertiaCams described above are operated using infrared (IR) LEDs as targets. However, we have also tested that they can work with any color of visible LEDs, or even with ultraviolet LEDs. This gives the flexibility to make the system compatible with night vision goggles that are frequently used in aircraft and ground vehicle cockpits, and invisible to enemy night vision devices. One option is the use of UV LEDs with built in black-window filters that block all the visible wavelengths (such as the Roithner Lasertechnik RLT370-110). This device when operated at low power produces almost no visible glow, and thus shares the advantage of an IR LED of not distracting the pilot.

A number of embodiments of the invention have been described. Nevertheless, it will be understood that various modifications may be made without departing from the spirit and scope of the invention.

What is claimed is:

1. A system for tracking the motion of an object relative to a moving reference frame, comprising:
   a first inertial sensor mounted on the tracked object;
   a second inertial sensor mounted on the moving reference frame;
   a third inertial sensor mounted on the moving reference frame and spaced apart from the second inertial sensor; and
   an element coupled to said first and second and third inertial sensors and configured to determine a position of the object relative to the moving reference frame based on signals from the first and second and third inertial sensors, wherein the determination of the position of the object includes determination of at least one component of an angular acceleration of the moving reference frame and wherein the determination of the annular acceleration is made by combining linear acceleration data from the second and third inertial sensors.

2. The system of claim 1, further comprising a non-inertial measuring subsystem for making independent measurements related to the position of the object relative to the moving reference frame, and a drift corrector using said independent measurements to correct drift that may occur in an inertial orientation integration.

3. The system of claim 2, in which the non-inertial measuring subsystem is selected from the set of optical, acoustic, magnetic, RF, or electromagnetic technologies.

4. The system of claim 3, in which the non-inertial measuring system is optical and involves measurement of the location of one or more targets in the image planes of one or more sensors.

5. The system of claim 4, where the targets emit radiation within a defined bandwidth about a central wavelength selected in the infrared, visible or ultraviolet region of an electromagnetic spectrum.

6. The system of claim 5, where the central wavelength is substantially invisible to night vision equipment.

7. The system of claim 5, where the central wavelength is substantially invisible to a human eye.

8. The system of claim 4, in which at least one optical sensor is mounted on the tracked object.

9. The system of claim 8, further comprising at least one optical sensor mounted rigidly with respect to the moving reference frame.

10. The system of claim 4, in which the optical system comprises two sensors mounted rigidly with respect to the moving reference frame, and separated by at least 10 centimeters.

11. The system of claim 10, in which the second inertial sensor is physically packaged with one of the optical sensors, and the third inertial sensor is physically packaged with the other optical sensor.

12. A system for tracking the motion of an object relative to a moving reference frame comprising:
a first inertial sensor mounted on the tracked object;
a second inertial sensor mounted on the moving reference frame;
a third inertial sensor mounted on the moving reference frame and spaced apart from the second inertial sensor;
an element coupled to said first and second and third inertial sensors and configured to determine a position of the object relative to the moving reference frame based on signals from the first and second and third inertial sensors; and
a drift corrector for correcting inertial drift in the determined position of the object with respect to the moving reference frame,
wherein the determination of the position of the object includes determination of at least one component of an angular acceleration of the moving reference frame and wherein the determination of the angular acceleration is made by combining linear acceleration data from the second and third inertial sensors.

13. The system of claim 12, where the drift corrector includes a Kalman filter.

14. A system for tracking the motion of an object relative to a moving reference frame comprising:
a first inertial sensor mounted on the tracked object;
a second inertial sensor mounted on the moving reference frame;
means coupled to said first and second inertial sensors for determining an orientation of the object relative to the moving reference frame based on signals from the first and second inertial sensors; and
a drift corrector for correcting inertial drift in the determined orientation of the object with respect to the moving reference frame, where the drift corrector includes a Kalman filter.

15. A method for tracking the motion of an object relative to a moving reference frame comprising:
mounting a first inertial sensor on the tracked object;
mounting a second inertial sensor on the moving reference frame;
determining an orientation of the object relative to the moving reference frame based on signals from the first and second inertial sensors; and
correcting inertial drift in the determined orientation of the object with respect to the moving reference frame, using a Kalman filter.

16. The system of claim 13, 14, or 15, or where the Kalman filter is configured to estimate biases of both the first and second inertial sensors, which become separately observable over time as the tracked object changes orientation relative to the moving reference frame.

17. A system for tracking the motion of an object relative to a moving reference frame comprising:
a tracking inertial measurement unit mounted on the tracked object;
three reference inertial measurement units mounted at three separated and non-collinear locations on the moving reference frame;
an element coupled to said tracking inertial measurement unit and to said reference inertial measurement units and configured to determine an orientation and a position of the object relative to the moving reference frame based on signals from the inertial measurement units; and
an element coupled to said reference inertial measurement units and configured to determine an angular acceleration of the moving reference frame based on the signals from the inertial measurement units.

18. The system of claim 17, where the determination of angular acceleration of the moving reference frame involves analysis of the differences of linear accelerations measured between each pair of separated reference inertial measurement units.

19. A system for tracking the motion of an object relative to a reference frame, comprising:
an optical sensor for measuring a location of a target in an image plane;
at least three light-emitting targets which emit invisible ultraviolet radiation which can be detected by the optical sensor but which does not interfere with night vision equipment;
an element coupled to said optical sensor and configured to determine a position of the object relative to the reference frame based on locations of the ultraviolet targets in the image plane of the optical sensor.

20. A system for tracking the motion of an object relative to a moving reference frame, comprising:
a first inertial sensor mounted on the tracked object;
a second inertial sensor mounted on the moving reference frame;
a third inertial sensor mounted on the moving reference frame and spaced apart from the second inertial sensor;

an element coupled to said first and second and third inertial sensors and configured to determine a position of the object relative to the moving reference frame based on signals from the first and second and third inertial sensors, and an optical measuring subsystem for making independent measurements related to the position of the object relative to the moving reference frame by measuring the location of one or more targets in the image planes of one or more sensors.

21. The system of claim 20, wherein the targets emit radiation within a defined bandwidth about a central wavelength selected in the infrared, visible or ultraviolet region of the electromagnetic spectrum.

22. The system of claim 21, wherein the central wavelength is substantially invisible to night vision equipment.

23. The system of claim 21, wherein the central wavelength is substantially invisible to the human eye.

24. A method for tracking the motion of an object relative to a moving reference frame, comprising:

mounting a first inertial sensor on the tracked object;

mounting a second inertial sensor on the moving reference frame;

mounting a third sensor mounted on the moving reference frame, spaced apart from the second inertial sensor; and coupling an element to said first and second and third inertial sensors, said element being configured to determine a position of the object relative to the moving reference frame based on the signals from the first and second and third inertial sensors, wherein the determination of the position of the object includes determination of at least one component of an angular acceleration of the moving reference frame and wherein the determination of the angular acceleration is made by combining linear acceleration data from the second and third inertial sensors.

25. The method of claim 24, further comprising providing a non-inertial measuring subsystem for making independent measurements related to the position of the object relative to the moving reference frame and using a drift corrector to correct drift that may occur in an inertial orientation integration, using said independent measurements.

26. The method of claim 25, wherein the non-inertial measuring subsystem is selected from the set of optical, acoustic, magnetic, RF, or electromagnetic technologies.

27. The method of claim 26, in which the non-inertial measuring system is optical and measures the location of one or more targets in the image planes of one or more sensors.

28. The method of claim 27, wherein the targets emit radiation within a defined bandwidth about a central wavelength selected in the infrared, visible or ultraviolet region of an electromagnetic spectrum.

29. The method of claim 28, where the central wavelength is substantially invisible to night vision equipment.

30. The method of claim 28, where the central wavelength is substantially invisible to a human eye.

31. The method of claim 27, in which at least one optical sensor is mounted on the tracked object.

32. The method of claim 31, further comprising mounting at least one optical sensor rigidly with respect to the moving reference frame.

33. The method of claim 27, in which the optical system comprises two sensors mounted rigidly with respect to the moving reference frame, and separated by at least 10 centimeters.

34. The method of claim 33, in which the second inertial sensor is physically packaged with one of the optical sensors, and the third inertial sensor is physically packaged with the other optical sensor.

35. A method for tracking the motion of an object relative to a moving reference frame comprising:

mounting a first inertial sensor on the tracked object;

mounting a second inertial sensor mounting on the moving reference frame;

mounting a third sensor on the moving reference frame and spacing it apart from the second inertial sensor;

coupling an element to said first and second and third inertial sensors, said element configured to determine a position of the object relative to the moving reference frame based on signals from the first and second and third inertial sensors; and using a drift corrector to correct inertial drift in a determined orientation of the object with respect to the moving reference frame, wherein the determination of the position of the object includes determination of at least one component of an angular acceleration of the moving reference frame and wherein the determination of the angular acceleration is made by combining linear acceleration data from the second and third inertial sensors.

36. The method of claim 35, where the drift corrector includes a Kalman filter.

37. A method for tracking the motion of an object relative to a moving reference frame comprising:

mounting a first inertial sensor on the tracked object;

mounting a second inertial sensor on the moving reference frame;

coupling to said first and second inertial sensors a device for determining an orientation of the object relative to the moving reference frame based on signals from the first and second inertial sensors; and using a drift corrector to correct inertial drift in the determined orientation of the object with respect to the moving reference frame, where the drift corrector includes a Kalman filter.

38. The method of claim 37, further comprising using the Kalman filter to estimate biases of both the first and second inertial sensors, which become separately observable over time as the tracked object changes orientation relative to the moving reference frame.

39. A method for tracking the motion of an object relative to a moving reference frame comprising:

mounting a tracking inertial measurement unit on the tracked object;

mounting three reference inertial measurement units mounted at three separated and non-collinear locations on the moving reference frame;

coupling an element to said tracking inertial measurement unit and to said reference inertial measurement units and, said element being configured to determine an orientation and a position of the object relative to the moving reference frame based on signals from the inertial measurement units; and coupling and element to said reference inertial measurement units, said element configured to determine an angular acceleration of the moving reference frame on the signals from the inertial measurement units.

40. The method of claim 39 where the determination of angular acceleration of the moving reference frame involves analysis of the differences of linear accelerations measured between each pair of separated reference inertial measurements units.

41. A method for tracking the motion of an object relative to a reference frame, comprising:

provinding an optical sensor for measuring a location of a target in an image plane;

providing at least three light-emitting targets which emit invisible ultraviolet radiation which can be detected by the optical sensor but which does not interfere with night vision equipment;

coupling an element to said optical sensor, said element configured to determine a position of the object relative to the reference frame based on locations of the ultraviolet targets in the image plane of the optical sensor.

42. A method for tracking the motion of an object relative to a moving reference frame, comprising:

mounting a first inertial sensor on the tracked object;

mounting a second inertial sensor on the moving reference frame;

mounting a third inertial sensor on the moving reference frame and spacing it apart from the second inertial sensor;

coupling an element to said first and second and third inertial sensors, said element being configured to determine a position of the object relative to the moving reference frame based on signals from the first and second and third inertial sensors, and using an optical measuring subsystem to make independent measurements related to the position of the object relative to the moving reference frame by measuring the location of one or more targets in the image planes of one or more sensors.

43. The method of claim 42, wherein the targets emit radiation within a defined bandwidth about a central wavelength selected in the infrared, visible or ultraviolet region of the electromagnetic spectrum.

44. The method of claim 43, wherein the central wavelength is substantially invisible to night vision equipment.

45. The method of claim 43, wherein the central wavelength is substantially invisible to the human eye.

* * * * *